United States Patent
Joo et al.

(10) Patent No.: US 10,570,087 B2
(45) Date of Patent: Feb. 25, 2020

(54) PSEUDO-CERAMIDE COMPOUND AND PREPARATION METHOD THEREFOR

(71) Applicant: AMOREPACIFIC CORPORATION, Seoul (KR)

(72) Inventors: Yung Hyup Joo, Yongin-si (KR); Jae Won Yoo, Yongin-si (KR); Yong Jin Kim, Yongin-si (KR); Ho Sik Rho, Yongin-si (KR); John Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/336,893

(22) PCT Filed: Sep. 14, 2017

(86) PCT No.: PCT/KR2017/010087
§ 371 (c)(1),
(2) Date: Mar. 26, 2019

(87) PCT Pub. No.: WO2018/062729
PCT Pub. Date: Apr. 5, 2018

(65) Prior Publication Data
US 2019/0248736 A1    Aug. 15, 2019

(30) Foreign Application Priority Data

Sep. 27, 2016 (KR) .................. 10-2016-0124064

(51) Int. Cl.
*C07C 235/06* (2006.01)
*C07C 231/02* (2006.01)
*C07B 51/00* (2006.01)
*C07D 319/06* (2006.01)

(52) U.S. Cl.
CPC ............ *C07C 235/06* (2013.01); *C07B 51/00* (2013.01); *C07C 231/02* (2013.01); *C07D 319/06* (2013.01); *Y02P 20/55* (2015.11)

(58) Field of Classification Search
CPC .................................................... C07C 231/02
USPC ......................................................... 564/183
See application file for complete search history.

(56) References Cited

U.S. PATENT DOCUMENTS

2015/0290099 A1   10/2015   Woo et al.
2017/0313648 A1   11/2017   Cho et al.

FOREIGN PATENT DOCUMENTS

| KR | 10-2005-0029785 A | 3/2005 |
| KR | 10-2008-0065086 A | 7/2008 |
| KR | 10-2014-0070474 A | 6/2014 |
| KR | 10-2016-0057760 A | 5/2016 |
| WO | 2014084676 A1 | 6/2014 |

OTHER PUBLICATIONS

International Search Report for Corresponding International Application No. PCT/KR2017/010087 (2 Pages) (dated Jan. 8, 2018).
Sharma et al., "Synthesis and Determination of Polymerization Rate Constants of Glucose-Based Monomers", Designed Monomers and Polymers, 2011, vol. 14, No. 5, pp. 499-513.

*Primary Examiner* — Ana Z Muresan
(74) *Attorney, Agent, or Firm* — Lucas & Mercanti, LLP

(57) ABSTRACT

The present invention relates to a pseudo-ceramide compound and a preparation method therefor. According to the present invention, the pseudo-ceramide compound has a molecular structure and a function similar to those of a natural ceramide, can be readily synthesized, and has excellent solubility in an organic solvent and excellent stability, and thus the pseudo-ceramide compound can be used as an alternative to a natural ceramide. Therefore, the pseudo-ceramide compound of the present invention can be widely applied to a skin preparation for external use, a cosmetic composition, and the like for reinforcing and maintaining a skin barrier function.

7 Claims, No Drawings

PSEUDO-CERAMIDE COMPOUND AND PREPARATION METHOD THEREFOR

CROSS REFERENCE TO RELATED APPLICATIONS

This application is a 371 of PCT/KR2017/010087, filed Sep. 14, 2017 which claims the benefit of Korean Patent Application No. 10-2016-0124064, filed Sep. 27, 2016, the contents of each of which are incorporated herein by reference.

TECHNICAL FIELD

The present invention relates to a novel pseudo-ceramide compound and a preparation method thereof.

BACKGROUND ART

The surface of human skin is protected by stratum corneum. Among the constituents of stratum corneum, stratum corneum intercellular lipid forms a lamella structure and contributes to maintain skin's basic function.

The stratum corneum intercellular lipid consists of ceramide, cholesterol, free fatty acid and the like. Among them, the ceramide is a main component and plays a central role in moisture retention and barrier function of the stratum corneum. It is known that if the content of ceramide in the stratum corneum is reduced, the protective barrier function of the stratum corneum is reduced and various skin diseases are exacerbated.

Meanwhile, it has been reported that if the stratum corneum is damaged by skin aging or external stimuli and thus the content of ceramide in the stratum corneum is reduced, the skin's lamella structure can be restored by supplementing ceramide from the outside and thus the skin can be restored to its normal state. Accordingly, for the purpose of restoring and maintaining skin barrier function and enhancing moisturizing power, the development of cosmetic composition containing the ceramide is actively being done.

The ceramide is extracted from various plants and animals containing the ceramide. However, the natural ceramide is not suitable for commercialization because it is difficult to mass-produce and the raw material is expensive due to difficulty of extraction and the like. In addition, the natural ceramide is low in solubility in various solvents used in cosmetics, and thus the natural ceramide is limited in the amount that can be used when preparing a product and there is a limit to obtaining efficacy.

Therefore, in order to replace the natural ceramide, it is necessary to research and develop a pseudo-ceramide compound which has a structure similar to the natural ceramide, is easy to synthesize, and has improved physical properties.

Prior Art Document (Patent Document 1) Korean Laid-open Patent Publication No. 2014-0070474, NOVEL PSEUDO-CERAMIDE COMPOUND AND METHOD FOR PREPARING THE SAME.

DISCLOSURE

Technical Problem

In order to solve the above problems, the present inventors have made efforts to synthesize a pseudo-ceramide compound having improved physical properties such as solubility while having a structure similar to the natural ceramide, and as a result, has completed the present invention.

Therefore, it is an object of the present invention to provide a novel pseudo-ceramide compound and a preparation method thereof.

Technical Solution

In order to accomplish the above object, the present invention provides a pseudo-ceramide compound represented by the following Chemical Formula 1:

[Chemical Formula 1]

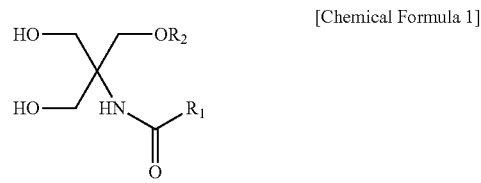

wherein $R_1$ and $R_2$ are as described in the specification.

In addition, the present invention provides a method for preparing a pseudo-ceramide compound, which is represented by the following Reaction Scheme 1 and comprises the steps of S1) introducing a protecting group into a compound of Chemical Formula 2 to prepare a compound of Chemical Formula 3;

S2) reacting the compound of Chemical Formula 3 with a compound of Chemical Formula 4 to prepare a compound of Chemical Formula 5;

S3) reacting the compound of Chemical Formula 5 with a compound of Chemical Formula 6 under a base catalyst to prepare a compound of Chemical Formula 7; and S4) removing the protecting group from the compound of Chemical Formula 7 to prepare a compound of Chemical Formula 1:

[Reaction Scheme 1]

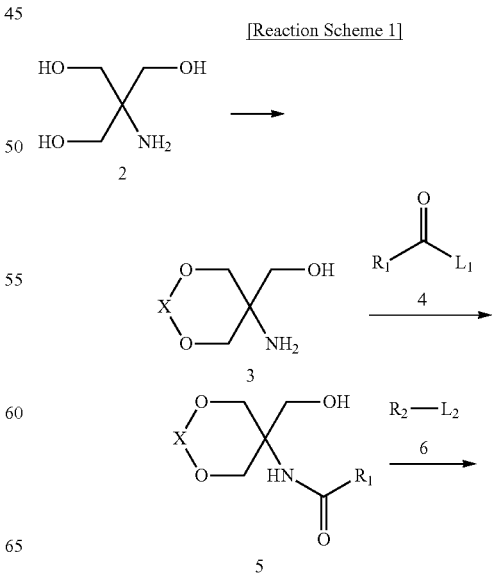

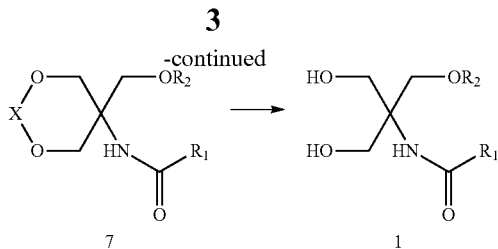

wherein X, $R_1$, $R_2$, $L_1$, and $L_2$ are as described in the specification.

Advantageous Effects

According to the present invention, the pseudo-ceramide compound has a molecular structure and a function similar to those of the natural ceramide, can be readily synthesized, and has excellent solubility and stability in an organic solvent, and thus can be used as an alternative to the natural ceramide. Therefore, the pseudo-ceramide compound of the present invention can be widely applied to a skin preparation for external use, a cosmetic composition, and the like for reinforcing and maintaining a skin barrier function.

BEST MODE

Hereinafter, the present invention will be described in detail so as to be easily carried out by those having ordinary skill in the art to which the present invention pertains. However, the present invention may be embodied in many different forms and should not be construed as limited to the embodiments set forth herein.

The present invention provides a novel pseudo-ceramide compound represented by the following Chemical Formula 1:

[Chemical Formula 1]

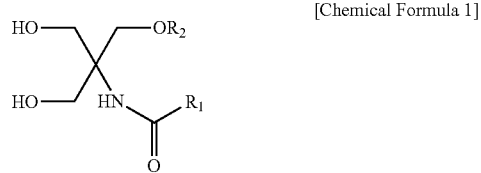

wherein $R_1$ and $R_2$ are the same as or different from each other and are each independently a C9 to C23 saturated or unsaturated aliphatic chain.

The C9 to C23 saturated aliphatic chain referred to in the present specification is a chain in which the carbon-carbon bond is composed of only single bonds, and may be, for example, but is not limited to, nonanyl (C9:0), decanyl (C10:0), undecanyl (C11:0), dodecanyl (C12:0), tridecanyl (C13:0), tetradecanyl (C14:0), pentadecanyl (C15:0), hexadecanyl (C16:0), heptadecanyl (C17:0), octadecanyl (C18:0), nonadecanyl (C19:0), icosanyl (C20:0), henicosanyl (C21:0), docosanyl (C22:0), or tricosanyl (C23:0).

In addition, the C9 to C23 unsaturated aliphatic chain referred to in the present specification is a chain including at least one carbon-carbon double or triple bond, and may be, for example, but is not limited to, nonenyl (C9:1), decenyl (C10:1), undecenyl (C11:1), dodecenyl(C12:1), tridecenyl (C13:1), tetradecenyl (C14:1), pentadecenyl (C15:1), hexadecenyl (C16:1), heptadecenyl (C17:1), octadecenyl (C18:1), nonadecenyl (C19:1), icosenyl (C20:1), henicosenyl (C21:1) docosenyl (C22:1), or tricosenyl (C23:1).

Preferably, $R_1$ and $R_2$ are the same as or different from each other, and each independently can be a C13 to C18 saturated or unsaturated aliphatic chain.

More preferably, $R_1$ and $R_2$ are the same as or different from each other, and each independently may be tridecanyl, tetradecanyl, pentadecanyl, hexadecanyl, heptadecanyl, or octadecanyl.

Furthermore preferably, $R_1$ may be tridecanyl, pentadecanyl, or heptadecanyl, and $R_2$ may be tetradecanyl, hexadecanyl, or octadecanyl.

Specific examples of the compound represented by Chemical Formula 1 may include hexadecanoic acid (2-hexadecyloxy-1,1-bis-hydroxymethyl-ethyl)-amide (Chemical Formula 8), hexadecanoic acid (1,1-bis-hydroxymethyl-2-tetradecyloxy-ethyl)-amide (Chemical Formula 9), hexadecanoic acid (1,1-bis-hydroxymethyl-2-octadecyloxy-ethyl)-amide (Chemical Formula 10), octadecanoic acid (2-hexadecyloxy-1,1-bis-hydroxymethyl-ethyl)-amide (Chemical Formula 11), octadecanoic acid (1,1-bis-hydroxymethyl-2-tetradecyloxy-ethyl)-amide (Chemical Formula 12), octadecanoic acid (1,1-bis-hydroxymethyl-2-octadecyloxy-ethyl)-amide (Chemical Formula 13), tetradecanoic acid (2-hexadecyloxy-1,1-bis-hydroxymethyl-ethyl)-amide (Chemical Formula 14), or tetradecanoic acid (1,1-bis-hydroxymethyl-2-octadecyloxy-ethyl)-amide (Chemical Formula 15).

[Chemical Formula 8]

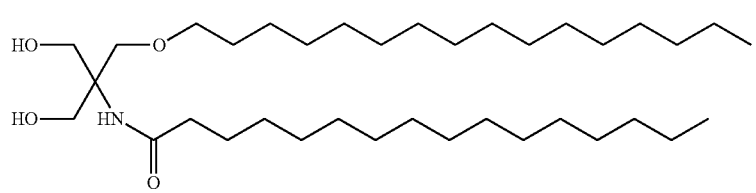

[Chemical Formula 9]

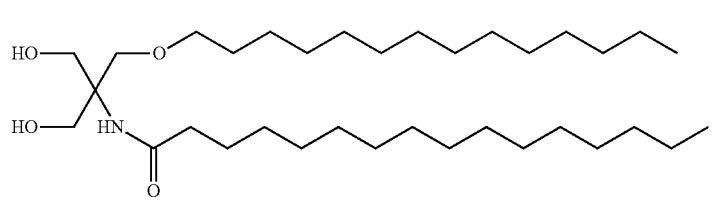

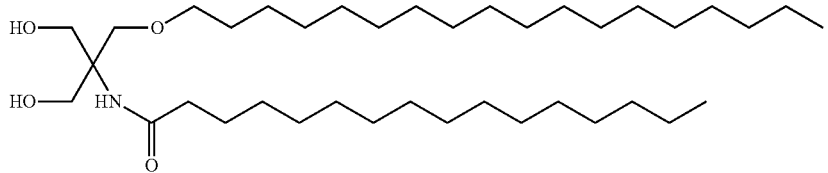
[Chemical Formula 10]

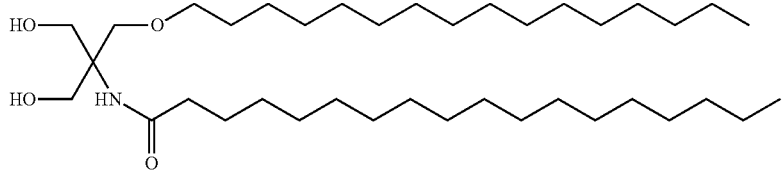
[Chemical Formula 11]

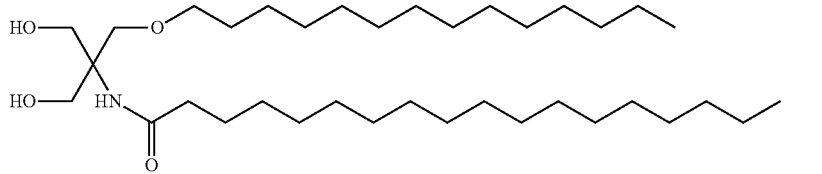
[Chemical Formula 12]

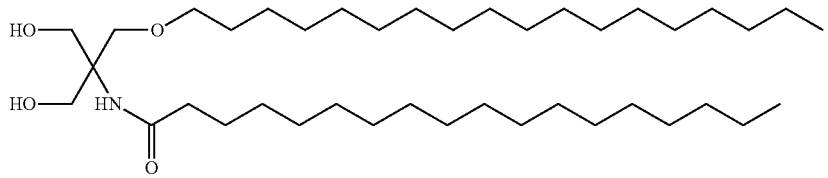
[Chemical Formula 13]

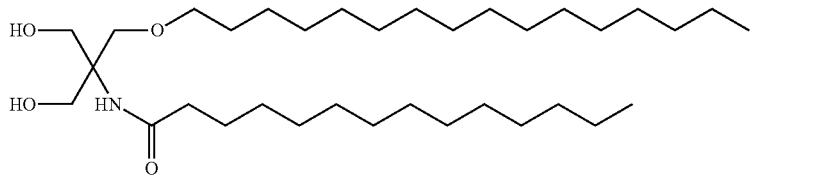
[Chemical Formula 14]

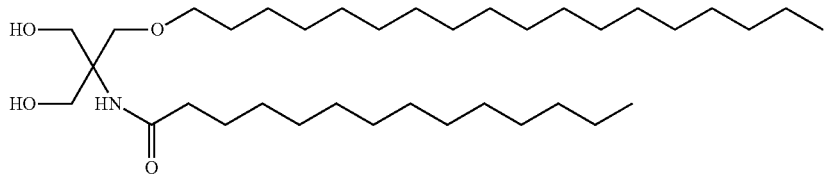
[Chemical Formula 15]

The pseudo-ceramide compound of Chemical Formula 1 as described above is structurally and functionally similar to the natural ceramide, and thus can be used as a raw material of the skin preparation for external use or cosmetic composition for skin barrier protection.

The pseudo-ceramide compound according to the present invention can be synthesized using 2-amino-2-hydroxymethyl-propane-1,3-diol as a starting material.

Specifically, the present invention provides a method for preparing the pseudo-ceramide compound, which is represented by the following Reaction Scheme 1 and comprises the steps of S1) introducing a protecting group into a compound of Chemical Formula 2 to prepare a compound of Chemical Formula 3;

S2) reacting the compound of Chemical Formula 3 with a compound of Chemical Formula 4 to prepare a compound of Chemical Formula 5;

S3) reacting the compound of Chemical Formula 5 with a compound of Chemical Formula 6 under a base catalyst to prepare a compound of Chemical Formula 7; and S4) removing the protecting group from the compound of Chemical Formula 7 to prepare a compound of Chemical Formula 1:

[Reaction Scheme 1]

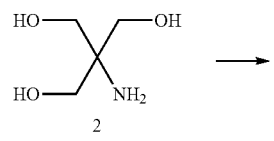

2

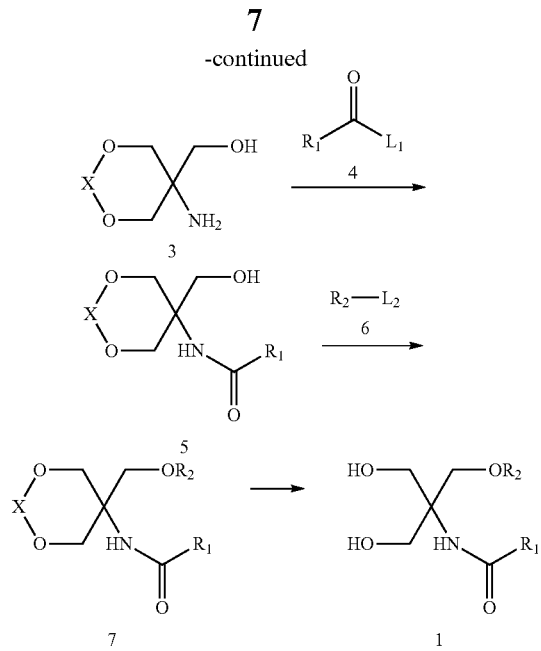

present invention, and a method known in the art can be used. For example, the isopropylidene ketal protecting group can be introduced by reacting tris (hydroxymethyl) aminomethane with 2,2-dimethoxypropane under a slightly acidic condition, as shown in the following Reaction Scheme 2.

[Reaction Scheme 2]

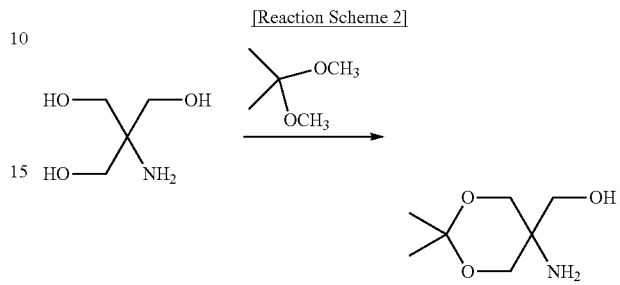

In the reaction of the above Reaction Scheme 2, the above-mentioned organic solvent may be used, and an acid catalyst may be used. Preferably, DMF as a solvent and p-toluene sulfonic acid (TsOH) as an acid catalyst can be used.

S2) Preparation of Compound of Chemical Formula 5

In step S2, the compound of Chemical Formula 3 prepared by introducing the protecting group in Step S1 is reacted with a compound of Chemical Formula 4 to prepare a compound of Chemical Formula 5 having an amide group.

The compound of Chemical Formula 4 is an acyl compound having a leaving group ($L_1$), and may be an acyl halide, an acid anhydride, or an ester. The compound of Chemical Formula 4 can be used without limitation as long as it satisfies the definition of Reaction Scheme 1 above, and for example, may be palmitoyl chloride ($CH_3(CH_2)_{14}COCl$), myristoyl chloride ($CH_3(CH_2)_{12}COCl$), stearoyl chloride ($CH_3(CH_2)_{16}COCl$) and the like.

The solvent used in this step is preferably the organic solvent as described above in Step S1, and if necessary, a basic catalyst such as triethylamine, N,N'-diisopropylethylamine, pyridine or N-methylmorpholine can be used. At this time, the reaction conditions, temperature, pressure, time and the like are not particularly limited, but are in accordance with known conditions.

According to one preferred embodiment of the present invention, dichloromethane as a solvent and triethylamine as a base catalyst can be used. The compound of Chemical Formula 5 can be prepared by adding the base catalyst to the compound of Chemical Formula 3 at 0° C., adding the compound of Chemical Formula 4 slowly thereto, and stirring at room temperature for 2 to 4 hours.

S3) Preparation of Compound of Chemical Formula 7

In step S3, an aliphatic chain is introduced into the hydroxy group of the compound of Chemical Formula 5 to prepare a compound of Chemical Formula 7 having a ceramide-like structure.

The compound of Chemical Formula 6, which is a reactant in this step, is a C9 to C23 alkyl halide, and can be used without limitation as long as it satisfies the definition of Reaction Scheme 1 above. Specifically, the compound of Chemical Formula 6 may be bromotetradecane, bromohexadecane, bromooctadecane or the like.

This step can be carried out using a solvent and a base catalyst used in the nucleophilic substitution reaction. Specifically, t-butanol, THF or 1,4-dioxane may be used as a wherein X is alkylidene, ethylidene, isopropylidene, cyclohexylidene, benzylidene or p-methoxybenzylidene, $R_1$ and $R_2$ are the same as or different from each other and are each independently a C9 to C23 saturated or unsaturated aliphatic chain, $L_1$ is Cl, Br, I, C1 to C4 acyloxy, or C1 to C4 alkoxy, and $L_2$ is Cl, Br, or I.

At this time, the C1 to C4 acyloxy may be formate, acetate, propionate or butanoate, and the C1 to C4 alkoxy may be methoxy, ethoxy, propoxy, isopropoxy or butoxy. Preferably, the $L_1$ is Cl.

Hereinafter, each step will be described in detail.

S1) Preparation of Compound of Chemical Formula 3

In step S1, a protecting group is introduced into tris (hydroxymethyl) aminomethane (2-amino-2-hydroxymethyl-propane-1,3-diol, Chemical Formula 2) to prepare a compound of Chemical Formula 3 in which 1,3-diols are protected.

The protecting group can be used without limitation as long as it is used as a protecting group of a hydroxy group. However, it is desirable to use a protecting group that is used as a diol protecting group so that two of the three hydroxy groups of tris (hydroxymethyl) aminomethane can be protected simultaneously. Specifically, methylidene acetal, ethylidene acetal, isopropylidene ketal, cyclohexylidene ketal, benzylidene ketal, or p-methoxybenzylidene acetal protecting group may be used.

The solvent used in this step is preferably an organic solvent, and for example, may be one selected from the group consisting of chloroform, dimethylformamide (DMF), dichloromethane, diisopropyl ether, diethylether, tetrahydrofuran (THF), dimethylacetamide (DMA), dimethyl sulfoxide (DMSO), chlorobenzene, toluene, benzene, acetone, and mixed solvents thereof.

In this step, a known acid or base catalyst may be used if necessary. The reaction conditions, temperature, pressure, time and the like are not particularly limited in the present invention, but are in accordance with known conditions.

According to one preferred embodiment of the present invention, the protecting group is an isopropylidene ketal protecting group. The method of introducing the isopropylidene ketal protecting group is not particularly limited in the solvent, and t-butoxide, potassium hydroxide, sodium hydroxide, lithium hydroxide or sodium hydride may be used as a base catalyst.

At this time, the reaction conditions, temperature, pressure, time and the like are not particularly limited in the present invention and can be appropriately controlled depending on the reactants used.

Specifically, in one embodiment of the present invention, t-butanol was used as a solvent, and potassium t-butoxide was used as a base catalyst, and the compound of Chemical Formula 7 was prepared by reacting at room temperature for 10 to 14 hours.

S4) Preparation of Compound of Chemical Formula 1

Step S4 is a step of removing the diol protecting group introduced in step S1, and the reaction conditions, temperature, pressure, time and the like are not particularly limited and may vary depending on the protecting group used. Specifically, the removal of the protecting group may be accomplished by treatment of the acidic aqueous solution, addition of hydrogen gas in the presence of a metal catalyst.

According to one preferred embodiment of the present invention, an acidic aqueous solution is used to remove the acetonide protecting group. At this time, the acid used may be hydrochloric acid, nitric acid, sulfuric acid, or acetic acid, preferably hydrochloric acid.

The conditions for the removal reaction of the protecting group are not particularly limited in the present invention, and the reaction is carried out at a temperature of −30 to 60° C., preferably −30 to 40° C. for 0.5 to 72 hours, preferably 1 to 12 hours.

The solvent may be a polar solvent capable of dissolving an acid, and may be one selected from the group consisting of water, C1-C4 lower alcohol, tetrahydrofuran and a mixed solvent thereof, preferably tetrahydrofuran.

The compound of Chemical Formula 1 prepared by the above-mentioned method can be applied to various fields, and can be widely applied to cosmetics, medicines, preparations for external use, foods and the like to which existing natural ceramide, synthetic ceramide or pseudo ceramide is applied.

MODE FOR INVENTION

Hereinafter, the present invention will be described in more detail with reference to the following Examples. However, the following Examples are for illustrative purposes only and are not intended to limit the scope of the present invention.

EXAMPLES

Example 1: Preparation of hexadecanoic acid (2-hexadecyloxy-1,1-bis-hydroxymethyl-ethyl)-amide (1) Preparation of hexadecanoic acid (5-hydroxymethyl-2,2-dimethyl-[1,3]dioxan-5-yl)-amide (Chemical Formula 16)

[Chemical Formula 16]

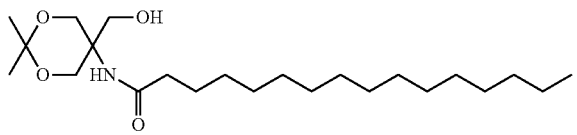

(5-amino-2,2-dimethyl-[1,3]dioxan-5-yl)-methanol (1.61 g), which was synthesized according to a method known in the literature (Helv. Chim. Acta 2003, 86, 2458-2470) using 2-amino-2-hydroxymethyl-propane-1,3-diol hydrochloride as starting material, was dissolved in dichloromethane (50 mL), and after adding triethylamine (1.7 mL), palmitoyl chloride (2.75 g) dissolved in dichloromethane (10 mL) while stirring at 0° C., was slowly added dropwise. The reaction solution was stirred at room temperature for 3 hours, and then washed with dilute hydrochloric acid solution and saturated sodium chloride solution. The organic solution layer was dried over anhydrous magnesium sulfate, filtered, concentrated under reduced pressure, and recrystallized from dichloromethane and hexane to obtain 2.5 g of a white solid.

$^1$H NMR (300 MHz, CDCl$_3$) δ 6.28 (brs, 1H), 5.18 (m, 1H), 3.83 (s, 4H), 3.65 (d, 2H, J=6.3 Hz), 2.28 (t, 2H, J=7.2 Hz), 1.65 ~1.25 (m, 32H), 0.88 (t, 3H, J=6.9 Hz).

(2) Preparation of hexadecanoic acid (2-hexadecyloxy-1,1-bis-hydroxymethyl-ethyl)-amide (Chemical Formula 8)

[Chemical Formula 8]

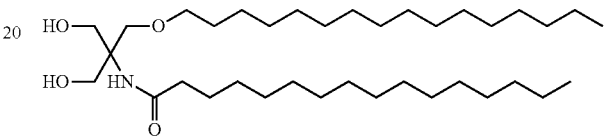

The hexadecanoic acid (5-hydroxymethyl-2,2-dimethyl-[1,3]dioxan-5-yl)-amide (2.0 g) prepared in the above (1) was dissolved in t-butanol (50 mL) and KOtBu (=potassium t-butoxide) (0.67 g) was slowly added thereto, followed by stirring at room temperature for 10 minutes. To this solution, bromohexadecane (1.53 g) was added, and further stirred for 12 hours. The reaction solution was neutralized with diluted hydrochloric acid to quench the reaction and extracted with dichloromethane. The organic layer was dried over anhydrous magnesium sulfate and then concentrated under reduced pressure. The reaction mixture was dissolved in tetrahydrofuran (20 mL), a 1 M aqueous hydrochloric acid solution (4 mL) was added, and the mixture was stirred at room temperature for 12 hours. The reaction solution was diluted with dichloromethane and washed with a saturated sodium hydrogen carbonate solution. The organic solution layer was dried over anhydrous magnesium sulfate and concentrated under reduced pressure. The product was isolated using column chromatography to obtain 0.88 g of the desired compound as a white solid.

$^1$H NMR (300 MHz, CDCl$_3$) δ 6.50 (brs, 1H), 4.34 (m, 2H), 3.71 ~3.45 (m, 8H), 2.55 (t, 2H, J=7.5 Hz), 1.80~1.20 (m, 54H), 0.88 (m, 6H).

Example 2: Preparation of hexadecanoic acid (1,1-bis-hydroxymethyl-2-tetradecyloxy-ethyl)-amide (Chemical Formula 9)

[Chemical Formula 9]

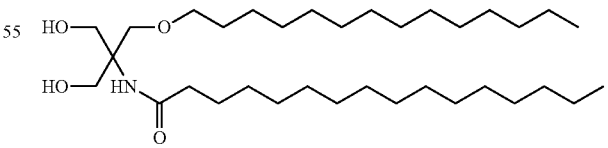

0.82 g of the desired compound was obtained using substantially the same method as in (2) of Example 1, except that bromotetradecane (1.39 g) was used instead of bromohexadecane (1.53 g).

$^1$H NMR (300 MHz, CDCl$_3$) δ 6.49 (brs, 1H), 4.32 (m, 2H), 3.71 ~3.43 (m, 8H), 2.42 (m, 2H), 1.80~1.05 (m, 50H), 0.87 (m, 6H).

Example 3: Preparation of hexadecanoic acid (1,1-bis-hydroxymethyl-2-octadecyloxy-ethyl)-amide

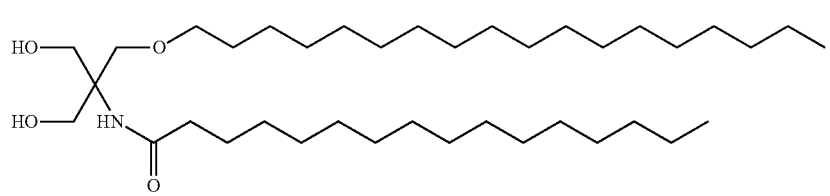

[Chemical Formula 10]

0.71 g of the desired compound was obtained using substantially the same method as in (2) of Example 1, except that bromooctadecane (1.67 g) was used instead of bromohexadecane (1.53 g).

$^1$H NMR (300 MHz, CDCl$_3$) δ 6.50 (brs, 1H), 4.33 (m, 2H), 3.71 ~3.44 (m, 8H), 2.24 (t, 2H, J=7.5 Hz), 1.80~1.20 (m, 58H), 0.88 (m, 6H).

Example 4: Preparation of octadecanoic acid (2-hexadecyloxy-1,1-bis-hydroxymethyl-ethyl)-amide (1) Preparation of octadecanoic acid (5-hydroxymethyl-2,2-dimethyl-[1,3]dioxan-5-yl)-amide (Chemical Formula 17)

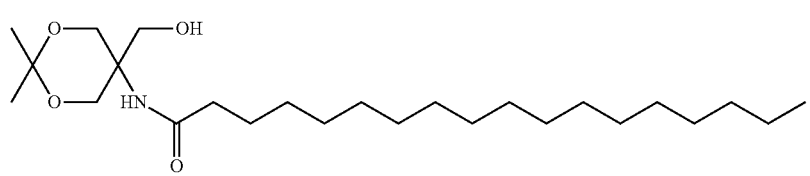

[Chemical Formula 17]

23 g of the desired compound as a white solid was obtained using substantially the same method as in (1) of Example 1, except that 12.8 g of (5-Amino-2,2-dimethyl-[1,3]dioxan-5-yl)-methanol was used as the starting material and stearoyl chloride (24.5 g) was used instead of palmitoyl chloride (2.75 g).

$^1$H NMR (300 MHz, CDCl$_3$) δ 6.28 (brs, 1H), 5.17 (m, 1H), 3.83 (s, 4H), 3.64 (d, 2H, J=6.0 Hz), 2.28 (t, 2H, J=7.5 Hz),1.65 ~1.25 (m, 36H), 0.87 (t, 3H, J=6.6 Hz).

(2) Preparation of octadecanoic acid (2-hexadecyloxy-1,1-bis-hydroxymethyl-ethyl)-amide (Chemical Formula 11)

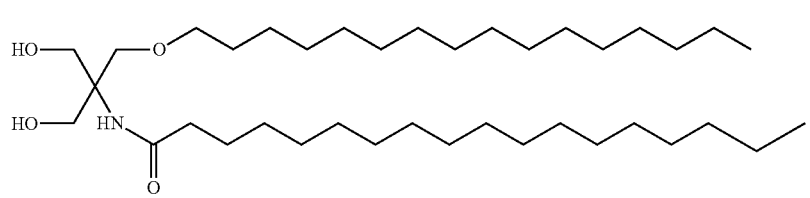

[Chemical Formula 11]

1.8 g of the desired compound was obtained using substantially the same method as in (2) of Example 1, except that octadecanoic acid (5-hydroxymethyl-2,2-dimethyl-[1,3]dioxan-5-yl)-amide (5.0 g) prepared in the above (1) was used instead of hexadecanoic acid (5-hydroxymethyl-2,2-dimethyl-[1,3]dioxan-5-yl)-amide, tetrahydrofuran (100 mL) was used instead of t-butanol, and KOtBu (1.73 g) and bromohexadecane (3.6 g) were used.

$^1$H NMR (500 MHz, CDCl$_3$) δ 6.48 (brs, 1H), 3.68~3.43 (m, 8H), 2.31 (m, 2H), 2.22 (m, 2H), 1.70~1.20 (m, 58H), 0.85 (m, 6H).

Example 5: Preparation of octadecanoic acid (1,1-bis-hydroxymethyl-2-tetradecyloxy-ethyl)-amide (Chemical Formula 12)

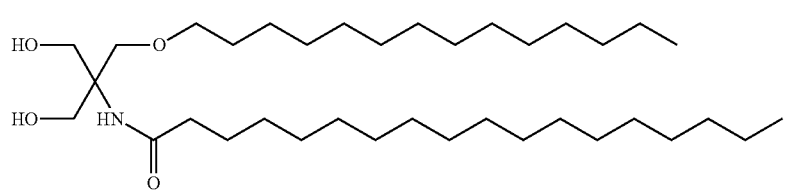

[Chemical Formula 12]

1.2 g of the desired compound was obtained using substantially the same method as (2) of Example 4, except that bromotetradecane (3.27 g) was used instead of bromohexadecane (3.6 g).

$^1$H NMR (500 MHz, CDCl$_3$) δ 6.47 (brs, 1H), 4.32 (m, 2H), 3.68~3.31 (m, 8H), 2.22 (m, 2H), 1.61~1.10 (m, 54H), 0.84 (m, 6H).

Example 6: Preparation of octadecanoic acid (1,1-bis-hydroxymethyl-2-octadecyloxy-ethyl)-amide (Chemical Formula 13)

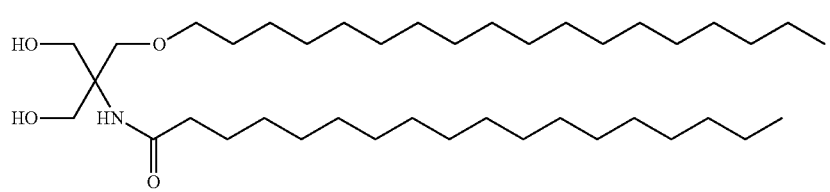

[Chemical Formula 13]

1.1 g of the desired compound was obtained using substantially the same method as in (2) of Example 4, except that bromooctadecane (3.14 g) was used instead of bromohexadecane (3.6 g), and octadecanoic acid (5-hydroxymethyl-2,2-dimethyl-[1,3]dioxan-5-yl)-amide (4.0 g) and KOtBu (1.38 g) were used.

$^1$H NMR (500 MHz, CDCl$_3$) δ 6.50 (brs, 1H), 3.70~3.40 (m, 8H), 2.26 (m, 2H), 1.90~1.15 (m, 64H), 0.88 (m, 6H).

Example 7: Preparation of tetradecanoic acid (2-hexadecyloxy-1,1-bis-hydroxymethyl-ethyl)-amide (1) Preparation of tetradecanoic acid (5-hydroxymethyl-2,2-dimethyl-[1,3]dioxan-5-yl)-amide (Chemical Formula 18)

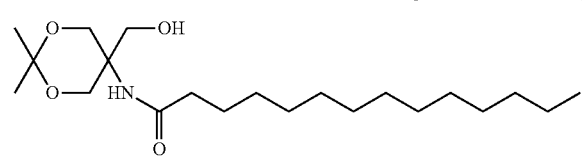

[Chemical Formula 18]

15 g of the desired compound as a white solid was obtained using substantially the same method as in (1) of Example 1, except that 12.8 g of (5-amino-2,2-dimethyl-[1,3]dioxan-5-yl)-methanol was used as the starting material and myristoyl chloride (19.5 g) was used instead of palmitoyl chloride (2.75 g).

$^1$H NMR (300 MHz, CDCl$_3$) δ 6.31 (brs, 1H), 5.20 (m, 1H), 3.85 (s, 4H), 3.67 (s, 2H), 2.31 (t, 2H, J=7.2 Hz), 1.68~1.28 (m, 28H), 0.90 (t, 3H, J =6.6 Hz).

(2) Preparation of tetradecanoic acid (2-hexadecyloxy-1,1-bis-hydroxymethyl-ethyl)-amide (Chemical Formula 14)

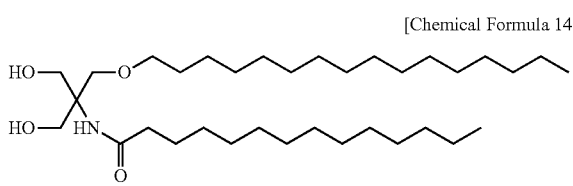 [SMILES: CCCCCCCCCCCCCCCCOCC(CO)(CO)NC(=O)CCCCCCCCCCCCC]

[Chemical Formula 14]

1.2 g of the desired compound was obtained using substantially the same method as in (2) of Example 1, except that tetradecanoic acid (5-hydroxymethyl-2,2-dimethyl-[1,3]dioxan-5-yl)-amide (3.71 g) as prepared in (1) above was used instead of hexadecanoic acid (5-hydroxymethyl-2,2-dimethyl-[1,3]dioxan-5-yl)-amide, tetrahydrofuran (100 mL) was used instead of t-butanol, and KOtBu (1.47 g) and bromohexadecane (2.74 g) were used.

$^1$H NMR (500 MHz, CDCl$_3$) δ 6.47 (brs, 1H), 4.22 (m, 2H), 3.68~3.32 (m, 8H), 2.24 (m, 2H), 1.80~1.10 (m, 50H), 0.86 (m, 6H).

Example 8: Preparation of tetradecanoic acid (1,1-bis-hydroxymethyl-2-octadecyloxy-ethyl)-amide (Chemical Formula 15)

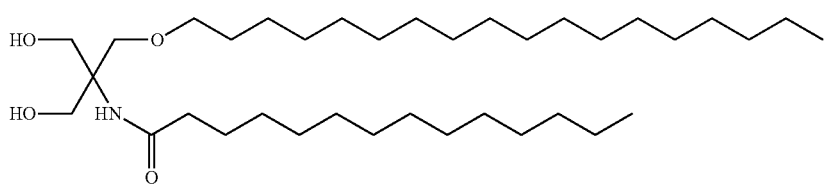

[Chemical Formula 15]

1.05 g of the desired compound was obtained using substantially the same method as in (2) of Example 7, except that bromooctadecane (3.3 g) was used instead of bromohexadecane.

$^1$H NMR (500 MHz, CDCl$_3$) δ 6.47 (brs, 1H), 4.31 (m, 2H), 3.68~3.43(m, 8H), 2.22 (t, 2H, J=7.0 Hz), 1.65~1.10 (m, 54H), 0.85 (m, 6H).

The invention claimed is:

1. A pseudo-ceramide compound of Chemical Formula 1:

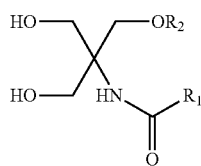

wherein R$_1$ and R$_2$ are the same as or different from each other and are each independently a C9 to C23 saturated or unsaturated aliphatic chain.

2. The pseudo-ceramide compound according to claim 1, wherein R$_1$ and R$_2$ are the same as or different from each other and are each independently a C13 to C18 saturated or unsaturated aliphatic chain.

3. The pseudo-ceramide compound according to claim 1, wherein the pseudo-ceramide compound is selected from the group consisting of hexadecanoic acid (2-hexadecyloxy-1,1-bis-hydroxymethyl-ethyl)-amide, hexadecanoic acid (1,1-bis-hydroxymethyl-2-tetradecyloxy-ethyl)-amide, hexadecanoic acid (1,1-bis-hydroxymethyl-2-octadecyloxy-ethyl)-amide, octadecanoic acid (2-hexadecyloxy-1,1-bis-hydroxymethyl-ethyl)-amide, octadecanoic acid (1,1-bis-hydroxymethyl-2-tetradecyloxy-ethyl)-amide, octadecanoic acid (1,1-bis-hydroxymethyl-2-octadecyloxy-ethyl)-amide, tetradecanoic acid (2-hexadecyloxy-1,1-bis-hydroxymethyl-ethyl)-amide, and tetradecanoic acid (1,1-bis-hydroxymethyl-2-octadecyloxy-ethyl)-amide.

4. A method for preparing a pseudo-ceramide compound, of Reaction Scheme 1 and comprises the steps of
    S1) introducing a protecting group into a compound of Chemical Formula 2 to prepare a compound of Chemical Formula 3;
    S2) reacting the compound of Chemical Formula 3 with a compound of Chemical Formula 4 to prepare a compound of Chemical Formula 5;
    S3) reacting the compound of Chemical Formula 5 with a compound of Chemical Formula 6 under a base catalyst to prepare a compound of Chemical Formula 7; and
    S4) removing the protecting group from the compound of Chemical Formula 7 to prepare a compound of Chemical Formula 1:

[Reaction Scheme 1]

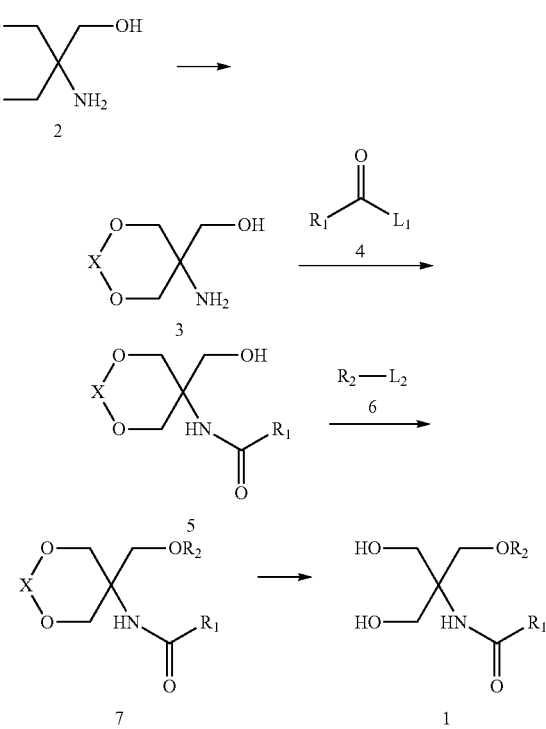

wherein X is selected from the group consisting of alkylidene, ethylidene, isopropylidene, cyclohexylidene, benzylidene and p-methoxybenzylidene,
R$_1$ and R$_2$ are the same as or different from each other and are each independently a C9 to C23 saturated or unsaturated aliphatic chain,
L$_1$ is selected from the group consisting of Cl, Br, I, C1 to C4 acyloxy, and C1 to C4 alkoxy, and
L$_2$ is selected from the group consisting of Cl, Br, and I.

5. The method for preparing the pseudo-ceramide compound according to claim 4, wherein the R$_1$ and R$_2$ are the same as or different from each other and are each independently a C13 to C18 saturated or unsaturated aliphatic chain.

6. The method for preparing the pseudo-ceramide compound according to claim 4, wherein the compound of Chemical Formula 4 selected from the group consisting of is myristoyl chloride, palmitoyl chloride, and stearoyl chloride.

7. The method for preparing the pseudo-ceramide compound according to claim 4, wherein the compound of Chemical Formula 6 selected from the group consisting of is bromotetradecane, bromohexadecane, and bromooctadecane.

\* \* \* \* \*